United States Patent [19]

Wessel et al.

[11] Patent Number: 5,705,674

[45] Date of Patent: Jan. 6, 1998

[54] PROCESS FOR PREPARING ORTHO-NITROBENZONITRILES

[75] Inventors: Thomas Wessel, Frankfurt; Peter Koch, Obertshausen, both of Germany

[73] Assignee: Hoechst Aktiengesellschaft, Germany

[21] Appl. No.: 698,792

[22] Filed: Aug. 16, 1996

[30] Foreign Application Priority Data

Aug. 16, 1995 [DE] Germany ............... 195 29 973.6

[51] Int. Cl.⁶ .................................................. C07C 253/14
[52] U.S. Cl. ................................................... 558/343
[58] Field of Search .......................................... 558/343

[56] References Cited

U.S. PATENT DOCUMENTS

| | | | |
|---|---|---|---|
| 2,195,076 | 3/1940 | Mannheim et al. | 260/465 |
| 4,886,936 | 12/1989 | Dinizo | 558/343 |
| 5,386,051 | 1/1995 | Beck et al. | 558/343 |

FOREIGN PATENT DOCUMENTS

| | | |
|---|---|---|
| 0097357 | 1/1984 | European Pat. Off. . |
| 0334188 | 9/1989 | European Pat. Off. . |
| 0496631 | 7/1992 | European Pat. Off. . |
| 0497765 | 8/1992 | European Pat. Off. . |
| 0608713 | 8/1994 | European Pat. Off. . |
| 2610675 | 9/1977 | Germany . |

OTHER PUBLICATIONS

Finger, G. C., et al., *J. M. Chem.* 78: 6034–6037 (1956).
Johnson, N. P., et al, *J. Chem. Soc.*: 1054–1067 (1964).
Dehmlow, E. V., *Angew. Chemie* 86: 187–197 (1974).
Maggini, M., et al, *Org. Chemie* 56: 6406–6411 (1991).
Gorvin, J. H., *J. Chem. Soc. Comm*: 972–975 (1976).

*Primary Examiner*—Johann Richter
*Assistant Examiner*—Ebenezer Sackey
*Attorney, Agent, or Firm*—Connolly and Hutz

[57] ABSTRACT

The present invention relates to a process for preparing ortho-nitrobenzonitriles of the formula I,

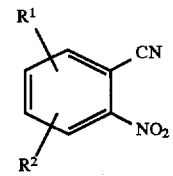

(I)

where $R^1$ and $R^2$ are as defined in claim 1, by reacting the corresponding ortho-fluoronitrobenzenes with alkali metal cyanides or cyanide-donating substances in the presence of phase transfer catalysts.

16 Claims, No Drawings

PROCESS FOR PREPARING ORTHO-NITROBENZONITRILES

The present invention relates to a process for preparing ortho-nitrobenzonitriles of the formula I,

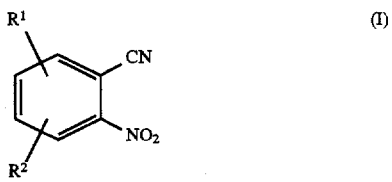

where $R^1$ and $R^2$ are hydrogen or electron-withdrawing groups, by reacting the corresponding ortho-fluoronitrobenzenes with a cyanide or a cyanide-donating substance.

The compounds of the formula I are, inter alia, important intermediates for the preparation of benzoic acid derivatives and alkyl benzoate derivatives, which in turn are important intermediates for the preparation of various active compounds, e.g. for the preparation of herbicides such as the compounds of EP-A-496 631 or isoxazole herbicides. Various processes for preparing ortho-nitrobenzonitriles of the formula I have already been described. In general, the corresponding ortho-chloronitrobenzenes are reacted with a heavy metal cyanide, in particular copper(I) cyanide, according to the Rosenmund-von Braun reaction. U.S. Pat. No. 2,195,076 describes, for example, halogen-cyanogen exchange reactions in which copper cyanide is employed at high temperatures in the presence of nitrogen bases such as pyridine or quinoline. In the case of copper-catalyzed halogen-cyanogen exchange reactions on the aromatic ring, the reactivity of the haloaromatic decreases distinctly in the order I>Br>Cl>> F (see, for example, J. Chem. Soc. 1964, 1097).

A significant disadvantage of this preparative method is that it requires the use of heavy metals such as copper. The removal of the heavy metals from the wastewater requires special measures. The reaction procedure unavoidably produces considerable amounts of heavy metal compounds as by-products, which have to be subjected to complicated work-up or have to be disposed of.

Sometimes, for example in the process described in EP-B-97 357, which is carried out at about 200° C., the preparation of benzonitriles by halogen-cyanogen exchange makes use not only of copper cyanide but also further copper salts such as copper(II) bromide, which additionally increases the formation of heavy metal salts.

EP-B-497 765 discloses a process for preparing ortho-nitrobenzonitriles from the corresponding ortho-chloronitrobenzenes in which alkali metal, alkaline earth metal or zinc bromides are added instead, but since the actual reagent is still copper cyanide or a mixture of copper (II) bromide and lithium cyanide, this procedure also results in formation of large amounts of heavy metal salts.

According to the process of DE-A-2 610 675, ortho-cyanoazo dyes can be obtained from the corresponding ortho-bromoazo dyes by carrying out the halogen-cyanogen exchange under phase transfer conditions using a mixture of copper or zinc cyanide with sodium or potassium cyanide. However, since the heavy metal cyanide can be only partially replaced by the alkali metal cyanide, this process too, like that of EP-A-334 188 in which the copper cyanide can be partially replaced by alkali metal cyanides, is still associated with considerable formation of heavy metal by-products.

Fluorine-cyanogen exchange on the aromatic ring using an alkali metal cyanide is described in U.S. Pat. No. 5,386,051 and EP-A-608 713. However, these documents each relate to only a single substance having a particular substituent combination, and the process procedure uses organic solvents which on transfer to the industrial scale require complicated measures in terms of equipment, for example for industrial hygiene reasons or for exclusion of moisture, and are economically unfavorable.

Although ortho-fluoronitrobenzenes are readily available via chlorine-fluorine exchange reactions (see, for example, J. Am. Chem. Soc. 78 (1956), 6034 and J. Org. Chem. 56 (1991), 6406), fluorine-cyanogen exchange reactions have hitherto been given little consideration for the preparation of the compounds of the formula I. This is attributable first and foremost to the fact that in the preparation of ortho-nitrobenzonitriles from ortho-fluoronitrobenzenes and alkali metal cyanides, the ortho-nitrobenzonitriles react further with the alkali metal cyanides in a Nef-type reaction to give cyanophenols (see J. Org. Chem. 40 (1975), 3748; cf. also J. Chem. Soc., Chem. Comm. 1976, 972).

A generally applicable, simple, economically favorable process for the preparation of compounds of the formula I in which no heavy metal compounds are obtained is still not available. It has now surprisingly been found that these compounds are obtainable in a favorable manner by fluorine-cyanogen exchange from the corresponding ortho-fluoronitrobenzenes using a cyanide or a cyanide-donating compound with phase transfer catalysis.

The present invention provides a process for preparing ortho-nitrobenzonitriles of the formula I,

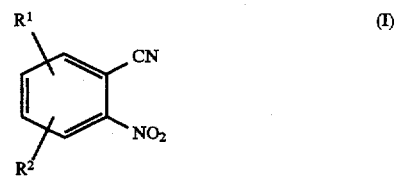

where $R^1$ and $R^2$, which can be identical or different, are hydrogen or electron-withdrawing groups, by reacting the corresponding ortho-fluoronitrobenzenes of the formula II,

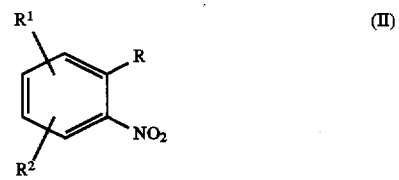

where $R^1$ and $R^2$ are as defined for the formula I, with alkali metal cyanides or cyanide-donating substances, wherein the reaction is carried out in an aqueous medium in the presence of phase transfer catalysts.

Examples of electron-withdrawing groups $R^1$ and $R^2$ are nitro, $(C_1-C_4)$-alkylsulfonyl, halo-$(C_1-C_4)$-alkylsulfonyl, cyano, carboxy, $((C_1-C_4)$-alkyl)oxycarbonyl, pentafluoroethyl and methyl monosubstituted, disubstituted or trisubstituted by halogen.

Alkyl groups can be straight-chain or branched. Suitable alkyl groups are, for example, methyl, ethyl, n-propyl, i-propyl, n-butyl, sec-butyl, i-butyl and tert-butyl. Preferred alkyl groups are methyl and ethyl, in particular methyl.

Examples of halogens are, in particular, fluorine, chlorine and bromine. Halogen is preferably fluorine or chlorine. Halo-$(C_1-C_4)$-alkylsulfonyl is, for example, chloromethylsulfonyl or 2-chloroethylsulfonyl. Examples of methyl monosubstituted, disubstituted or trisubstituted by halogen are chloromethyl, dichloromethyl, trichloromethyl, fluoromethyl, difluoromethyl or trifluoromethyl, in particular trifluoromethyl.

A particularly preferred electron-withdrawing group is the trifluoromethyl group.

If one or both of the radicals $R^1$ and $R^2$ are electron-withdrawing groups, these can be located in any positions relative to the nitro group and the cyano group (or the nitro group and the fluorine atom). Preferably, one of the two radicals $R^1$ and $R^2$ is hydrogen and the other is an electron-withdrawing group or both radicals $R^1$ and $R^2$ are electron-withdrawing groups. Particularly preferably, one of the two radicals $R^1$ and $R^2$ is hydrogen and the other is an electron-withdrawing group. In this particularly preferred embodiment of the present invention, the electron-withdrawing group is preferably also in the para position to the fluorine atom in the formula II or to the cyano group in the formula I.

Examples of alkali metal cyanides are lithium cyanide, sodium cyanide, potassium cyanide, rubidium cyanide and cesium cyanide, with sodium and potassium cyanide being preferred.

As cyanide-donating compounds, preference is given to using cyanohydrins of the formula III,

(III)

where $R^3$ is hydrogen or a straight-chain or branched alkyl group, preferably a $(C_1-C_8)$-alkyl group, particularly preferably a $(C_1-C_4)$-alkyl group, and $R^4$ is a straight-chain or branched alkyl group, preferably a $(C_1-C_8)$-alkyl group, particularly preferably a $(C_1-C_4)$-alkyl group, which can be the same as the alkyl group $R^3$ or can be different therefrom. Examples of $(C_1-C_4)$-alkyl groups are the groups already mentioned above, additional examples of $(C_1-C_8)$-alkyl groups are pentyl, hexyl, heptyl and octyl. Very particularly preferably, $R^3$ and $R^4$ are both methyl.

In the process of the invention, it is possible to use one or more alkali metal cyanides or one or more cyanide-donating compounds of the formula III, likewise mixtures containing one or more alkali metal cyanides in addition to one or more compounds of the formula III.

The reaction of the invention can be carried out either in a purely aqueous medium, i.e. only water is used as solvent, dispersing medium or diluent, or in an organic-aqueous medium, i.e. one or more inert organic solvents, dispersing media or diluents are used in addition to water. The mixing ratio of water and organic solvent can, like the total amount of water and any solvent, vary within wide limits and depends on the individual case. The organic solvents can be miscible with water or be readily or sparingly soluble therein. The reaction medium can consist of one or more phases. However, it is here also possible when using a single-phase reaction medium, for example also when using a purely aqueous medium, for a multiphase system to occur in the presence of the starting substances and/or products. An organic solvent is advantageously added particularly when the starting compound of the formula II is not liquid under the reaction conditions. If an aqueous-organic medium is used, preferred solvents, dispersing media or diluents are aprotic dipolar solvents, alcohols and nonpolar solvents. Examples of suitable aprotic dipolar solvents (for definition, see, for example, Chem. Rev. 69 (1969), 1–32) are N,N-dimethylformamide, N,N-dimethylacetamide, dimethyl sulfoxide and N-methylpyrrolidone. Alcohols suitable as solvents are, for example, methanol, ethanol, n-propanol, i-propanol, n-butanol or ethylene glycol monomethyl ether.

Suitable nonpolar solvents are preferably aliphatic and aromatic hydrocarbons and hydrocarbon mixtures such as hexane, heptane, cyclohexane, methylcyclohexanes, toluene, xylene or petroleum fractions, and also chlorinated hydrocarbons. However, it is also possible to use other solvents, for example ketones such as acetone or ethyl methyl ketone or ethers or carboxylic esters such as ethyl acetate or butyl acetate. Toluene is particularly preferred as solvent. However, the reaction is very particularly preferably carried out in a purely aqueous medium without addition of an organic solvent.

Suitable phase transfer catalysts (see, for example, Angewandte Chemie 86 (1974), 187 or W. P. Weber and G. W. Gokel, Phase Transfer Catalysis in Organic Synthesis, Springer Verlag Berlin, Heidelberg, New York 1977) are generally, for example, the halides such as fluorides, chlorides, bromides and iodides, the cyanides, the hydroxides, the hydrogensulfates, the $(C_1-C_4)$-alkylsulfates, in particular methylsulfates and ethylsulfates, or the tetrafluoroborates of quaternary nitrogen compounds and phosphonium compounds. Particularly suitable phase transfer catalysts are also compounds having crown ether properties such as benzo[15]crown-5 or [18]crown-6-tetracarboxylic acid, or, as an example of an open-chain crown ether, tris-(3,6-dioxaheptyl)amine.

Examples of groups having a quaternary nitrogen atom which can be present in the phase transfer catalysts are tetra-$(C_1-C_4)$-alkylammonium such as tetraethylammonium, tetrapropylammonium, tributylmethylammonium and tetrabutylammonium; tetraalkylammonium having one or more longer-chain alkyl radicals such as tetrahexylammonium, tetraoctylammonium, methyltrioctylammonium, hexadecyltrimethylammonium and ethylhexadecyldimethylammonium; cycloalkylammonium such as cyclohexyldiethyl-n-butylammonium; aralkylammonium such as tri-$(C_1-C_4)$-alkyl)benzylammonium, $(C_1-C_6)$-alkylbenzyldimethylammonium, benzyltrimethylammonium, benzyltriethylammonium, benzyltributylammonium, benzylcyclohexyldiethylammonium, benzyldi-n-propylethylammonium, benzyldi-n-butylethylammonium, benzylbutylcyclohexylethylammonium, dibenzyldi-n-propylammonium, dibenzyldi-n-butylammonium, cyclohexyldibenzylethylammonium, dibutylethylphenethylammonium, benzylnonyldibutylammonium-, benzyldecyldibutylammonium and benzyldodecyldimethylammonium; ammonium groups having hydroxy or alkoxy radicals such as butyldi (2-methoxyethyl)ethylammonium, di-n-butyldi-(2-methoxyethyl)ammonium, n-butyl(2-methylbutyl)di(2-methoxyethyl)ammonium, di(2-methoxyethyl)di-n-propylammonium, di(2-methoxyethyl)diamylammonium, benzyldi(2-methoxyethyl)ethylammonium, benzyl-n-butyldi(2-methoxyethyl)ammonium, dibenzyldi-(2-methoxyethyl)ammonium and N-dodecyl-N-methylephedrinium; groups derived from nitrogen heterocycles such as morpholinium ions, pyrrolidinium ions, piperidinium ions and hexamethyleniminium ions, N,N-dimethyl-morpholinium, N,N-di(n-butyl)morpholinium, N-benzyl-N-ethylmorpholinium, N-benzyl-N-hexylmorpholinium, N,N-di(n-butyl)pyrrolidinium, N-benzyl-N-(n-butyl)pyrrolidinium, N,N-dibenzylpyrrolidinium, N-(n-butyl)-N-ethylpiperidinium, N-benzyl-N-(n-butyl)piperidinium, N-benzyl-N-(2-ethylhexyl)piperidinium, N-benzyl-N-(n-butyl)-2-ethylpiperidinium, N-benzyl-N-(n-butyl)-2-(n-butyl)-2- ethylpiperidinium, N,N-dibenzylhexamethyleniminium, N-benzyl-N-isobutylhexamethyleneiminium, N-(n-butyl)-N-isobutylhexamethyleneiminium, N-benzyl-N-(n-butyl)-3,3,5-trimethylhexamethyleniminium, N-benzyl-N-(2-(n-butoxy)-propyl)hexamethyleniminium and N-benzylquininium; groups having 2 quaternary nitrogen atoms such as 1,ω-diammonioalkanes, 1,ω-di(morpholin-4-ylio)alkanes, 1,ω-di(pyrrolidin-1-ylio)alkanes, 1,ω-di(piperidin-1-ylio)alkanes, 1,ω-di(hexamethylenimin-1-ylio)alkanes, 1,6-di(benzylbutylethylammonio)-hexane, 1,8-di(N-benzylpyrrolidin-1-ylio)octane, 1,6-di(N-ethylpiperidin-1-ylio)hexane, 1,8-di-(N-(n-butyl)piperidin-1-ylio)octane and 1,6-di(N-benzylhexamethylenimin-1-ylio)hexane.

The phosphonium salts usable as phase transfer catalyst can contain alkyl and aryl groups. Examples of suitable phosphonium groups are tetrabutylphosphonium, tributylhexadecylphosphonium, ethyltrioctylphosphonium, butyltriphenylphosphonium and tetraphenylphosphonium.

The phase transfer catalysts are commercially available or can easily be prepared by known methods or by analogy to known methods, e.g. by quaternization of tertiary amines. The phase transfer catalysts can be used as solid or as solution; they are preferably used in the usually obtainable form, ammonium hydroxides, for example, as solution, and with the usually obtainable anion. However, if desired, the anion can first be replaced by generally known methods. The reaction can be carried out with a single phase transfer catalyst or with mixtures of two or more phase transfer catalysts, including commercially available industrial mixtures of such compounds.

Preferred phase transfer catalysts are tetra(($C_1$–$C_6$)alkyl)ammonium and tri-(($C_1$–$C_4$)alkyl)benzylammonium salts with halide or hydrogensulfate as anion and also tetra($C_1$–$C_6$)alkyl)phosphonium salts with halide as anion. Particular preference is given to tetra(n-butyl)ammonium salts, in particular the hydrogensulfate, chloride and bromide, and tetra(n-butyl)phosphonium salts, in particular the bromide. Furthermore, from the group of phase transfer catalysts having crown ether properties, particular preference is given to tris-(3,6-dioxaheptyl)amine.

Some of the ortho-fluoronitrobenzenes of the formula II used as starting substances are commercially available. If necessary, they can be prepared by known procedures or by analogy with known procedures, e.g. by the methods described in J. Am. Chem. Soc. 78 (1956), 6034 and J. Org. Chem. 56 (1991), 6406. The compounds of the formula III are also mostly commercially available or can easily be prepared by known methods.

The procedure in the preparation according to the invention of the benzonitriles of the formula I from the fluorine compounds of the formula II corresponds to the customary techniques of organic chemistry. The exact way in which the preparation is carried out and the reaction conditions depend on the individual case. The order in which the components are combined is generally as desired. For example, all components, the starting substance of the formula II, the alkali metal cyanide and/or the cyanide-donating substance, the phase transfer catalyst, the water and any further solvents and auxiliaries, can be placed in the reaction vessel and the reaction can then be carried out under the desired conditions for the desired period of time. However, it is also possible, for example, to initially charge the reaction vessel with the compound of the formula II as such or together with water and/or, if desired, further solvents and to add thereto, in one or more portions or continuously, the alkali metal cyanide, preferably in the form of a solution, and/or the cyanide-donating substance, as such or in dissolved or diluted form.

In this procedure, the phase transfer catalyst can be initially charged in the reaction vessel or be metered in, either separately or, for example, dissolved in the alkali metal cyanide solution. Likewise, for example, the alkali metal cyanide and/or the cyanide-donating substance can be initially charged together with the phase transfer catalyst, water and if desired further solvents and auxiliaries and the compound of the formula II can be added thereto, as such or in dissolved or diluted form, in one or more portions or continuously. The reaction is then usually carried out while stirring at the desired temperature and, if desired, with single, multiple or continuous addition of auxiliaries or reactants, until the desired degree of reaction has been achieved. The process of the invention can be carried out not only batchwise, i.e. discontinuously, but also continuously, for example in cascades of stirred vessels or in a tube reactor.

The mixing ratios of the components depend on the individual case. In general, based on the ortho-fluoronitrobenzene of the formula II, the alkali metal cyanide or the cyanide-donating substance is used in excess, alkali metal cyanides in, for example, a 1- to 6-fold, preferably a 1.5- to 5-fold, particularly preferably a 2- to 4-fold molar amount, cyanide-donating substances of the formula III in, for example, a 1- to 6-fold, preferably a 1.5- to 5-fold, particularly preferably a 1.5- to 3.5-fold amount.

The amount of the phase transfer catalyst can be varied within wide limits and is usually a 0.005- to 2-fold molar amount, based on the ortho-fluoronitrobenzene of the formula II, preferably a 0.01- to 1-fold, particularly preferably a 0.01- to 0.5-fold molar amount.

It is often favorable to set a certain pH range depending on the individual case by addition of acid or base. Generally, the reaction is carried out in the neutral or alkaline range, preferably at pH values of from 7 to 12, particularly preferably at pH values of from 7.5 to 11.5. Furthermore, when using alkali metal cyanides, preference is given to a pH of from 9 to 11, in particular from 10 to 11; when using cyanide-donating substances of the formula III, preference is given to a pH of from 7 to 10, in particular from 7 to 8. A particular pH can be set at the beginning of the reaction. Portionwise or continuous addition of acid or base also enables the pH to be held at a certain value or within a certain range during the entire reaction procedure. To set the pH, use is generally made of the customary acids and bases in the form of a solution of appropriate concentration, for example hydrochloric acid, sulfuric acid, phosphoric acid, sodium hydroxide solution or potassium hydroxide solution. Addition of a buffer system also enables a particular pH range to be maintained.

The reaction is normally carried out at atmospheric pressure or a slightly superatmospheric pressure, e.g. at a gage pressure of up to 3 bar, but it can equally well be carried out at higher gage pressures. The reaction temperature is usually from 0° C. to 100° C., preferably from 20° C. to 100° C., particularly preferably from 20° C. to 90° C., very particularly preferably from 20° C. to 80° C. The temperature can also be changed while carrying out the reaction, for example it can first be held at a relatively low value and be increased at the end to complete the reaction. The reaction can be carried out until the starting compounds of the formula II are substantially consumed, but it is often favorable to allow it to proceed only to a certain degree of reaction dependent on the individual case, then work up the reaction mixture and reuse recovered starting substance of the formula II in the next batch.

The work-up of the reaction mixture to isolate the compounds of the formula I can be carried out in a customary manner by isolation or separation methods known per se, for example by filtration, centrifugation, phase separation, extraction, salting out, (vacuum) distillation, steam distillation or chromatographic methods. It can also be favorable to first set a certain pH for the work-up or to make use of the principle of pH separation, or to first admix the reaction mixture with water or to first evaporate it completely or partially or, for example, to distill off organic solvents completely or partially. The method used in the individual case depends, for example, on the physical properties of the compounds, e.g. on the melting and boiling point and the solubility. Isolation is preferably carried out by means of phase separation, if appropriate after addition of an organic solvent, and distillation steps; the combination of steam distillation and subsequent vacuum distillation is particularly preferred for, in particular, the separation of unreacted starting substance of the formula II and product of the formula I. The product of the formula I thus obtained in a simple manner generally contains only small amounts of impurities and can be used in subsequent reactions without further purification. If desired, it can be further purified in a conventional manner. If the reaction was not carried out to complete conversion of the starting substance of the formula II, starting substances recovered in the work-up or mixtures of starting substance and product obtained can generally be directly reused in a new batch. The wastewater obtained from the reaction needs only to be subjected to a treatment to destroy cyanide or cyanide-donating substances present and can then be conveyed, for example, to a conventional wastewater purification plant. Since the process of the invention makes it possible to avoid using heavy metals such as copper in the halogen-cyanogen exchange, complicated measures for removal of heavy metals from the wastewater and the disposal or reprocessing of the heavy metal wastes become unnecessary.

EXAMPLES

Example 1

6 g of tetrabutylammonium hydrogensulfate are added to a solution of 29.5 g of sodium cyanide in 200 ml of water. The mixture obtained is carefully adjusted to a pH of 10.5 using 30 ml of 0.5N sulfuric acid and then admixed with 52 g (0.25 mol) of 4-fluoro-3-nitrobenzotrifluoride. The mixture is heated to 60° C. and stirred for 1 hour at this temperature, with the pH being maintained in the range from 9.5 to 10.5 by addition of 0.05N sulfuric acid. After this time, gas-chromatographic analysis of the reaction mixture indicates a content of 57% of 2-nitro-4-trifluoromethylbenzonitrile and 36% of 4-fluoro-3-nitrobenzotrifluoride.

To isolate the product, the organic and aqueous phases of the reaction mixture are, after cooling to room temperature, separated from one another in a separating funnel. The organic phase is steam distilled to remove the starting substance. The organic phase is separated from the distillate of the steam distillation. This gives 18.1 g of a mixture which, according to gas-chromatographic analysis, comprises 79% of 4-fluoro-3-nitrobenzotrifluoride and 15% of 2-nitro-4-trifluoromethylbenzonitrile and which can be fed directly to a subsequent batch. The product is isolated from the residue of the steam distillation, after removal of the water, by vacuum distillation via a short Vigreux column. Distillation at 20 mbar and a temperature at the top of 148°–150° C. gives 28.2 g of product which, according to gas-chromatographic analysis, contains 92% of 2-nitro-4-trifluoromethylbenzonitrile and 1% of 4-fluoro-3-nitrobenzotrifluoride.

Example 2

A solution of 5.9 g of sodium cyanide and 0.5 g of tetrabutylphosphonium bromide in 50 ml of water, which has previously been adjusted to a pH of 10.5 using 5 ml of 0.5N hydrochloric acid, is added dropwise to 10.5 g (0.05 mol) of 4-fluoro-3-nitrobenzotrifluoride at 65° C. while stirring over a period of 1 hour. Otherwise, the reaction is carried out in a similar manner to Example 1. After a reaction time of 4 hours, gas-chromatographic analysis of the reaction mixture shows a content of 61% of 2-nitro-4-trifluoromethylbenzonitrile and 33% of 4-fluoro-3-nitrobenzotrifluoride.

Example 3

Using a method similar to Example 2, a solution of 6 g of sodium cyanide and 1 g of tris(3,6-dioxaheptyl)amine (TDA) in 40 ml of water, which has previously been adjusted to a pH of 10.5 using 5 ml of 0.5N hydrochloric acid, is added dropwise to 10.5 g (0.05 mol) of 4-fluoro-3-nitrobenzotrifluoride at 60° C. After reaction time of 6 hours, 40% of 2-nitro-4-trifluoromethylbenzonitrile and 53% of starting substance are present.

Example 4

A solution of 12 g of sodium cyanide and 3 g of benzyltriethylammonium chloride in 80 ml of water is carefully adjusted a pH of 10.8 using 12 ml of 0.5N hydrochloric acid. To this solution there is added dropwise, at 60° C. over a period of 1 hour, a mixture of 10.5 g (0.05 mol) of 4-fluoro-3-nitrobenzotrifluoride and 20 ml of toluene. Otherwise, the reaction is carried out in a similar manner to Example 1. After a reaction time of 1.5 hours, the gas chromatogram shows a content of 11% of 2-nitro-4-trifluoromethylbenzonitrile and 86% of 4-fluoro-3-nitrobenzotrifluoride.

Example 5

A mixture of 63 g (0.3 mol) of 4-fluoro-3-nitrobenzotrifluoride, 42 g of acetone cyanohydrin, 1 g of tetrabutylammonium hydrogensulfate and 200 ml of water is heated to 80° C. and stirred at this temperature for 5 hours, with the pH being maintained at from 7 to 7.5 by dropwise addition of a total of 25 ml of 2N sodium hydroxide solution. After 5 hours, 30% of 2-nitro-4-fluoromethylbenzonitrile and 65% of 4-fluoro-3-nitrobenzotrifluoride are present according to gas-chromatographic analysis.

We claim:

1. A process for preparing an ortho-nitrobenzontrile of the formula I,

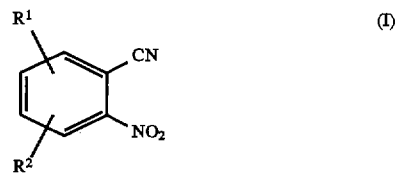

where $R^1$ and $R^2$, which can be identical or different, are hydrogen or electron—withdrawing groups, which comprises reacting the corresponding ortho-fluoronitrobenzene of the formula II,

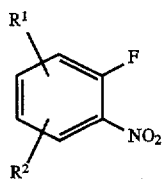

(II)

where $R^1$ and $R^2$ are as defined for the formula I, with an alkali metal cyanide or a cyanide-donating substance, wherein the reaction is carried out in an aqueous medium in the presence of a phase transfer catalyst.

2. The process as claimed in claim 1, wherein $R^1$ and $R^2$ are, independently of one another, hydrogen, nitro, $(C_1-C_4)$-alkylsulfonyl, halo-$(C_1-C_4)$-alkylsulfonyl, cyano, carboxy, $((C_1-C_4)$-alkyl)oxycarbonyl, pentafluoroethyl or methyl monosubstituted, disubstituted or trisubstituted by halogen.

3. The process as claimed in claim 1, wherein one of the radicals $R^1$ and $R^2$ is hydrogen and the other is trifluoromethyl.

4. The process as claimed in claim 1, wherein the ortho-nitrobenzonitrile prepared is 2-nitro-4-trifluoromethylbenzonitrile.

5. The process as claimed in claim 1, wherein the reaction is carried out using sodium or potassium cyanide.

6. The process as claimed in claim 1, wherein the cyanide-donating substance used is a cyanohydrin of the formula III

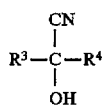

(III)

where $R^3$ is hydrogen or a straight-chain or branched alkyl group, and $R^4$ is a straight-chain or branched alkyl group which can be the same as or different than the alkyl group of $R^3$.

7. The process as claimed in claim 6, wherein $R^3$ and $R^4$ are a $(C_1-C_8)$-alkyl group.

8. The process as claimed in claim 6, wherein $R^3$ and $R^4$ are both methyl.

9. The process as claimed in claim 1, wherein the phase transfer catalyst is a salt of a quaternary nitrogen compound or phosphonium compound.

10. The process as claimed in claim 9, wherein the phase transfer catalyst is a tetra(n-butyl)ammonium salt or tetra (n-butyl)phosphonium salt.

11. The process as claimed in claim 10, wherein the phase transfer catalyst is the hydrogen sulfate salt of tetra(n-butyl) ammonium or the bromide salt of tetra(n-butyl) phosphonium.

12. The process as claimed in claim 1, wherein the phase transfer catalyst is a compound having crown ether properties.

13. The process as claimed in claim 12, wherein the phase transfer catalyst is tris(3,6-dioxaheptyl)amine.

14. The process as claimed in claim 1, wherein the reaction is carried out in a purely aqueous medium without addition of an organic solvent.

15. The process as claimed in claim 1, wherein the reaction is carried out at a pH of from 7 to 12.

16. The process as claimed in claim 1, wherein the reaction is carried out at a temperature of from 0° C. to 100° C.

* * * * *